United States Patent [19]

Song et al.

[11] Patent Number: 5,514,380

[45] Date of Patent: May 7, 1996

[54] BIODEGRADABLE HYDROGEL COPOLYMER AS DRUG DELIVERY MATRIX

[75] Inventors: Soo S. Song; Ho H. Kim, both of Tae Jeon; Yil W. Yi, Chon Ju, all of Rep. of Korea

[73] Assignee: Sam Yang Co., Ltd., Seoul, Rep. of Korea

[21] Appl. No.: 268,915

[22] Filed: Jun. 30, 1994

[30] Foreign Application Priority Data

May 17, 1994 [KR] Rep. of Korea .................. 1994-10696

[51] Int. Cl.[6] ........................................ A61F 2/00
[52] U.S. Cl. .................. 424/426; 424/428; 424/486; 514/965
[58] Field of Search .................. 424/426, 428, 424/486

[56] References Cited

U.S. PATENT DOCUMENTS

| 5,041,292 | 8/1991 | Feijen | 424/484 |
| 5,330,768 | 7/1994 | Park et al. | 424/501 |

Primary Examiner—Thurman K. Page
Assistant Examiner—William E. Benston, Jr.
Attorney, Agent, or Firm—Kenyon & Kenyon

[57] ABSTRACT

This invention concerns the thermoplastic, biodegradable hydrogel copolymer which is easily degraded and excreted in human body by the hydrolysis of intramolecular ester and amide bond. The structure of present copolymer comprises i) hydrophilic and swellable soft domain consisting of polyethyleneoxide (PEO), and ii) hydrophobic, biodegradable, crystallizable and non-swellable hard domain consisting of polylactide (PLA), polyglycolide (PGA), polylactide-glycolide (PLGA) and polycaprolactone (PCL).

5 Claims, No Drawings

BIODEGRADABLE HYDROGEL COPOLYMER AS DRUG DELIVERY MATRIX

BACKGROUND OF THE INVENTION

1. Field of the Invention

The present invention relates to a novel thermoplastic, biodegradable multi-block hydrogel copolymer used for drug delivery matrix, having both hydrophobic blocks and hydrophilic blocks. More specifically, this invention concerns a thermoplastic, biodegradable hydrogel copolymer which is easily degraded and excreted in the human body by the hydrolysis of intramolecular ester and amide bonds. The structure of present copolymer comprises i) a hydrophilic and swellable soft domain consisting of polyethyleneoxide (PEO), and ii) a hydrophobic, biodegradable, crystallizable and non-swellable hard domain consisting of polylactide (PLA), polyglycolide (PGA), polylactideglycolide (PLGA) and polycaprolactone (PCL).

2. Description of the Prior Art

Recently, drug delivery systems for regulating drug release to a specific site within the range of a constant effective dose has been researched very actively. For this purpose, biomedical polymers have been developed as a drug delivery matrix. However, biomedical polymers developed so far have some drawbacks as follows:

i) It is difficult to use biomedical polymers for delivering the drugs having a high molecular weight;

ii) Physical treatment is required for removing non-biodegradable copolymers, if such non-biodegradable copolymers are used for a drug delivery matrix; and iii) In case of hydrogels developed up to now, these materials have very low processibility due to their crosslinked nature. Furthermore, these materials cannot be used easily as a drug delivery matrix due to their toxicity to the human body.

To solve the above mentioned drawbacks, the inventors have researched thermoplastic, biodegradable hydrogel copolymers having the following properties:

i) the copolymers can be easily processed into appropriate preparations by simple processing methods, such as, infusion processing methods or solvent casting methods, since there is no chemical crosslinkage in the copolymers; and ii) the copolymers can be easily degraded into small and nontoxic molecules by simple hydrolysis or enzyme hydrolysis in order to be easily excreted through the kidney.

Biodegradable copolymers disclosed until now are aliphatic polyester, polyorthoester, polyanhydride, poly α-amino acid, polyphosphagen, polyalkylcyanoacrylate. Among the aliphatic polyesters, polylactide (PLA), polyglycolide (PGA) and polylactideglycolide (PLGA) have been approved as copolymers nontoxic to humans by the FDA. These copolymers have been applied as drug delivery devices to carry the drugs having small molecular weight.

Recently, polypetides or proteins produced by cell engineering or recombinant DNA technology have been approved as major medicines. However, these medicines have been administered only by injection, because these medicines are water-soluble and are very unstable macromolecular compounds with a short half-life. Therefore, finding another suitable delivery route for these compounds becomes a major research subject.

The application of aliphatic polyesters as a delivery system for protein drugs has some handicaps owing to their difficulties in loading process, complicated release mechanism, low degradability and their hydrophobic properties. Therefore, the improved degradable materials have been required as a drug delivery matrix for protein drugs.

Block copolymers as a drug delivery matrix are disclosed by U.S. Pat. No. 4,942,035. These copolymers are block copolymers in the shape of PLA/PEO/PLA or PGA/PEO/PGA which comprise polyethyleneoxide as a hydrophilic block and polylactide (D-, L- or DL-form), polyglycolide, poly-ε-caprolactone or poly-3-hydroxybutylic acid as a hydrophobic block. However, these block copolymers have some drawbacks, for example, they are difficult to excrete from the human body, because they use too high molecular weight PEO.

On the other hand, diblock and triblock copolymers having polyalkyleneoxide, polyglycolide and trimethylene carbonate are disclosed by U.S. Pat. No. 4,716,203. These block copolymers were invented for coating materials, and contain some materials which are not easily degraded and toxic to human body.

Other block copolymers having polyethylene glycol as a hydrophilic component and polylactide as a hydrophobic component are reported in J. Pol. Sci. (A): Vol. 27,2151(1989), J. Pol. Sci. (A): Vol. 39,1(1990), J. Applied. Poly. Sci.: Vol. 50, 1391 (1993) and J. Applied. Poly. Sci.: Vol. 51,473 (1994). However, these copolymers were prepared by simple copolymerization of the two components to be used as drug delivery matrix.

SUMMARY OF THE INVENTION

The object of the present invention is to provide a multiblock copolymer used for a drug delivery matrix which has improved biodegradability and nontoxicity to the human body without having intramolecular crosslinkage.

Multi-block copolymers of the present invention used for a drug delivery matrix are prepared by the synthesis of a hydrophilic and swellable soft domain (A—), and a hydrophobic, biodegradable, crystallizable and non-swellable hard domain (B - - - ).

Multiblock coopolymers of the present invention can be illustrated by the following formulas (I)a, (I)b, (l)c, (I)d, (I)e and (I)f

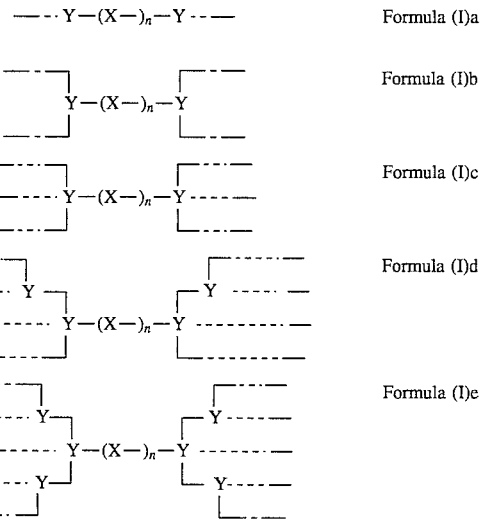

-continued $$[\underline{\overline{\phantom{---}}}\ Y-(X-)_n-O]_q-C \quad \text{Formula (I)f}$$

wherein

A(—) represents a hydrophilic, non-biodegradable, and swellable polymers essentially consisting of polyethyleneoxide(PEO) and/or a copolymer of PEO/polypropyleneoxide (PPO);

B(- - -) represents a hydrophobic, biodegradable, crystallizable, and non-swellable polymers essentially consisting of polylactide(PLA), polyglycolide (PGA), a copolymer of PLA/PGA, polycaprolactone, polyorthoester and/or polyanhydride;

X represents a biodegradable chemical linkage, such as an amide linkage, ester linkage, and/or carbonate linkage;

Y represents a chemical linkage between block (A) and block (B), or block (B) and block (B), such as an amide linkage, ester linkage, and/or carbonate linkage;

n represents an integer 0 to 10;

q represents an integer 3 to 4.

DETAILED DESCRIPTION OF THE INVENTION

As hydrophilic, non-biodegradable polymers, polyethyleneoxide and/or copolymers of PEO/PPO of M.W. 600–30,000, preferably 2,000–10,000, can be used. The polymers less than M.W. 2,000 show low flexibility and processiblility, and the polymers more than M.W. 10,000 are difficult to excrete through the kidney.

To solve the excretion difficulties of large molecular polyethyleneglycol (PEG), biodegradable polyethyleneglycol derivatives having high flexibility and processibility have been synthesized in the present invention. In other words, the hydrophilic block having biodegradable linkage (X—)has been obtained by the polymerization steps:

i) a hydrophilic polymer, such as PEO and/or PEO/PPO, is anionized by an initiator, such as potassium naphthalene, sodium naphthalene, lithium diisopropylate, potassium-t-butylate, sodium-t-butylate, sodium hydroxide and/or potassium hydroxide;

ii) a required amount of hydrophobic monomer, such as glycolide, lactide or caprolactone, is added and polymerized into the both anion ends of hydrophilic polymer; and iii) a required amount of ethyleneoxide is added and polymerized into the anion ends of the copolymer obtained above.

The hydrophilic block having biodegradable linkage (X—) as obtained above has particular properties that are desirable for a drug delivery matrix:

i) high processibility of high molecular weight PEG, and ii) high biodegradability into small molecules to be easily excreted through kidney.

As hydrophobic, biodegradable, crystallizable and non-swellable polymers, polylactide (PLA), polyglycolide (PGA), polycaprolactone (PCL), and/or their copolymers can be used. Copolymers having a various number of branches can be obtained by the chemical linkage (Y) between block (A) and block (B).

The preferred type of block copolymers of the present invention can be illustrated by the following formula (I) and (I')

$$H-O(CH_2)_z-(OCHR_1COOCHR_2CO)_m]_r-Y-A-Y'-\\ [(COCHR_1OC(=O)\ CHR_2O)_m-O(CH_2)_z-H]_l \quad (I)$$

$$[H-O(CH_2)_z-(O(CH_2)_5CO)_m]_r-Y-A-Y'-[(CO(CH_2)_5O)_m\\ -O(CH_2)_z-H]_l \quad (I')$$

wherein

A represents a hydrophilic multi-block copolymer as $[(CH_2CH_2O)_n-X-(OCH_2CH_2)_n]_r$;

X represents $-O(COCH_2O)_x-$, $-[COCH(CH_3)O]_x-$;

Y represents $-CH_xNHCO-$;

Y' represents $-CONHCH_y-$;

$R_1$ and $R_2$ represents each independently hydrogen or methyl;

x represents the integer 1 to 10;

z represents the integer 1 to 5;

y represents the integer 0, 1 or 2;

l represents the integer 1, 2 or 3;

m represents the integer 1 to 100;

n represents the integer 20 to 500;

k represents the integer 0 to 10; and r represents the integer 0 to 10.

The preparation method for the multi-block copolymers of the present invention can be explained as follows.

1 Eq. of normal polyethyleneoxide (PEO) of M.W. 600–20,000 is placed in a well-dried reactor, and dissolved in THF solvent. Thereafter, 0.05N– 0.5N of potassium-naphthalene solution is added to the reactor. When the potassium-naphthalene solution is added in the same equivalent amount of hydroxyl groups of PEO, the color of the solution disappears from pale green.

At the same time as the color disappearance, a required amount of hydrophobic monomer, such as glycolide or lactide, is added and polymerized. Thereafter, a required amount of ethyleneoxide is added and polymerized. Then, the hydrophilic block having biodegradable linkage (X—) is obtained.

1 Eq. of hydrophilic block having biodegradable linkage (X—) obtained above and 2.5 Eq. of p-nitrophenylchloroformate (NPC) or carbonyl diimidazole (CDI) are dissolved in organic solvent. Thereafter, 2.5 Eq. of base, such as triethylamine or pyridine, is added and reacted.

Reacted material is filtered and added to non-polar solvent. The hydrophilic block having biodegradable linkage (X—), both ends hydroxyl groups of which is protected by NPC, is precipitated. After drying the obtained polymer, the polymer is reacted with tris(hydroxyalkyl) aminomethane in polar solvent. After precipitation of reacted material in non-polar solvent, various kinds of hydrophilic block polymers having both ends hydroxyl groups are obtained. The hydroxyl groups of these block polymers show the NMR proton peaks in at 3.22 ppm.

1 Eq. of well-dried block polymer obtained above is laid on reactor, and dissolved in THF solvent. Thereafter, 0.05–0.5N of potassium-naphthalene solution is added to the reactor. When the potassium-naphthalene solution is added in the same equivalent amount of hydroxyl groups of block polymer, the color of the solution disappears from pale green.

At the same time of color disappearance, a required amount of glycolide or lactide, monomer of hydrophobic block, is added and polymerized. Thereafter, a required amount of ethyleneoxide is added and polymerized. Finally, the biodegradable hydrogel copolymer of the present invention is obtained. The obtained hydrogel copolymer as above anion polymerization method shows better physical properties than the copolymer by conventional coupling polymerization method.

As described above, the multi-block copolymer of the present invention comprises i) hydrophilic block which is linked by biodegradable linkage among PEOs and/or copolymers of PEO/PPO, and ii) hydrophobic block comprises PLA, PGA, PGLA, PCL and/or their copolymers.

By changing the M.W. or components of each block, various types of thermoplastic, biodegradable hydrogel copolymers can be prepared. Therefore, various copolymers can be easily synthesized according to the present invention.

The present invention can be explained more specifically by following examples, but it is not limited by following examples.

EXAMPLE 1

1 mmole of polyethylene glycol (PEG) of M.W. 3350 was placed in a well-dried dried reactor, and dissolved in 200 ml of dried THF solvent. Thereafter, 2 mmole of 0.1N potassium-naphthalene solution was added to the reactor. When the color disappeared from pale green, 8 mmole of L-lactide dissolved in THF solvent was added. After reacting for 30 minutes, 0.1 mole of distilled ethyleneoxide (EO) was added under nitrogen atmosphere, and stirred for one week. A small quantity of acetic acid dissolved in ether was added for finishing the reaction. After precipitating in cool methanol, the precipitated material was left in a refrigerator for one day, and the obtained material was filtered and dried in a vacuum.

1 mmole of the compound obtained above, 2 mmole of triethylamine and 100 ml of acetonitrile were placed on a well-dried reactor, and stirred. With stirring, 5 mmole of p-nitrophenylchloroformate (NPC) dissolved in acetonitrile was added and stirred for 24 hours. After filtration for removing the salt, the reacted solution was poured to ether. Then, the reacted material was precipitated. After filtering and drying the reacted material in a vacuum, multiblock PEO [(NPC-PEO-PLA)$_2$-PEO] was obtained.

0.1 mmole of the NPC-multiblock PEO obtained above, 0.2 mmole of tris (hydroxymethyl) aminomethane and DMSO as solvent were mixed and reacted for 24 hours. The reacted material was precipitated in ether, and the precipitated material was dissolved in water. After extracting using chloroform, the block polymer having hydroxyl groups at both ends was obtained. The hydroxyl groups of the obtained polymer show an NMR proton peak at 3.30 ppm (DMSO-d$_6$). The number average molecular weight of the obtained copolymer was 9,000.

EXAMPLE 2

0.1 mmole of the Tris-multiblock PEO obtained in example 1 was placed in a well-dried reactor, and dissolved in THF solvent. Then, 0.6 mmole of 0.1 N-potassium naphthalene solution was added. When the color of the solution disappeared from pale green, 24 mmole of L-lactide dissolved in THF was added. After reacting for 30 minutes, 0.3 mole of distilled ethyleneoxide (EO) was added under nitrogen atmosphere, and stirred for one week. A small quantity of acetic acid dissolved in ether was added for finishing the reaction. After precipitating in cool methanol, the precipitated material was left in a refrigerator for one day, and the obtained material was filtered and dried in vacuum.

The NMR proton peaks of the lactide of the obtained copolymer appeared at 5.19 and 1.55 ppm, and the proton peak of oxyethylene (—CH$_2$CH$_2$O—) appeared at 3.65 ppm. The number average molecular weight was 25,000.

EXAMPLE 3

The copolymer was obtained with the process of example 1 except that 4 mmole of L-lactide was used. The molecular weight of the obtained copolymer was 8,400.

EXAMPLE 4

The copolymer was obtained with the process of example 2 except that 0.1 mmole of the obtained copolymer of example 3 (M.W.=8,400) and 12 mmole of L-lactide were used. The number average molecular weight of the obtained copolymer was 23,300.

EXAMPLE 5

The copolymer was obtained with the process of example 1 except that 1 mmole of polyethyleneglycol (PEG) (M.W.= 4,600) was used. The molecular weight of the obtained copolymer was 10,000.

EXAMPLE 6

0.1 mmole of the copolymer obtained in example 5 (M.W.=10,000) was placed in a well-dried reactor, and dissolved in THF solvent. Then, 0.6 mmole of 0.1N potassium-naphthalene solution was added. Finally, the copolymer was obtained with the process of example 1. The NMR proton peaks of the lactide of the obtained copolymer appeared at 5.20 and 1.52 ppm. The number average molecular weight was 26,500.

EXAMPLE 7

The copolymer was obtained with the process of example 1 except that 1 mmole of polyethyleneglycol (PEG) (M.W.= 4,600) and 4 mmole of L-lactide were used. The molecular weight of the obtained copolymer was 9,800.

EXAMPLE 8

The copolymer was obtained with the process of example 2 except that 0.1 mmole of the obtained copolymer of example 7 (M.W.=9,800) and 12 mmole of L-lactide were used. The NMR proton peaks of the lactide of the obtained copolymer appeared at 5.19 and 1.55 ppm, and the number average molecular weight of the obtained copolymer was 24,900.

EXAMPLE 9

1 mmole of potassium-pentaerythrol was placed in a well-dried reactor, and 100 ml of dried toluene was added. Thereafter, 0.2 mole of distilled ethyleneoxide(EO) was added under nitrogen atmosphere, and stirred for one week. A small quantity of acetic acid dissolved in ether was added for finishing the reaction. After precipitating in cool methanol, the precipitated material was left in a refrigerator for one day, and the obtained material was filtered and dried in vacuum.

1 mmole of the compound obtained above, 2 mmole of triethylamine and 100 ml of acetonitrile were placed in a well-dried reactor, and stirred. With stirring, 5 mmole of p-nitrophenylchloroformate (NPC) dissolved in acetonitrile was added and stirred for 24 hours. After filtration for removing the salt, the reacted solution was poured to ether. Then, the reacted material was precipitated. After filtering and drying the reacted material in a vacuum, multiblock PEO [(NPC-PEO-PLA-PEO-CH$_2$)$_4$C] was obtained.

0.1 mmole of the NPC-multiblock PEO obtained above, 0.4 mmole of tris (hydroxymethyl) aminomethane and DMSO as solvent were mixed and reacted for 24 hours. After precipitating in ether, the block polymer was obtained. The proton peak of the methylene radical of the pentaerythrol was detected at 4.20 ppm, the proton peaks of the lactide were detected at 5.16 ppm and 1.56 ppm, and the proton peak of the hydroxyl group was detected at 3.20 ppm. The molecular weight of the obtained copolymer was 20,000.

EXAMPLE 10

The copolymer was obtained with the process of example 2 except that 0.1 mmole of the obtained copolymer of example 9 (M.W.=20,000) and 32 mmole of L-lactide and 6.4 mole of ethylenoxide were used. The number average molecular weight of the obtained copolymer was 41,000.

EXAMPLE 11

The copolymer was obtained with the process of example 9 except that 0.08 mole of ethyleneoxide was used. The molecular weight of the obtained copolymer was 9,500, and the NMR proton peaks of this copolymer are same as those of example 9.

EXAMPLE 12

The copolymer was obtained with the process of example 2 except that 0.1 mmole of the obtained copolymer of example 11 (M.W.=9,500) and 32 mmole of L-lactide were used. The number average molecular weight of the obtained copolymer was 17,500.

EXAMPLE 13

The copolymer was obtained with the process of example 1 except that 8 mmole of glycolide was used. The molecular weight of the obtained copolymer was 8,400.

EXAMPLE 14

The copolymer was obtained with the process of example 2 except that 0.1 mmole of the obtained copolymer of example 13 (M.W.=8,400) and 12 mmole of glycolide were used. The number average molecular weight of the obtained copolymer was 23,000.

EXAMPLE 15

1 mmole of polyethylene glycol (PEG) of M.W. 3350 was placed in a well-dried reactor, and dissolved in 200 ml of dried THF solvent. Thereafter, 2 mmole of 0.1N potassium-naphthalene solution was added to the reactor. When the color disappeared from pale green, 8 mmole of glycolide dissolved in THF solvent was added. After reacting for 30 minutes, 0.1 mole of distilled ethyleneoxide (EO) was added under nitrogen atmosphere, and stirred for one week. A small quantity of acetic acid dissolved in ether was added for finishing the reaction. After precipitating in cool methanol, the precipitated material was left in a refrigerator for one day, and the obtained material was filtered and dried in a vacuum.

1 mmole of the compound obtained above, 2 mmole of triethylamine and 100 ml of acetonitrile were placed in a well-dried reactor, and stirred. With stirring, 5 mmole of p-nitrophenylchloroformate (NPC) dissolved in acetonitrile was added and stirred for 24 hours. After filtration for removing the salt, the reacted solution was poured to ether. Then, the reacted material was precipitated. After filtering and drying the reacted material in a vacuum, multiblock PEO [(NPC-PEO-PGA)$_2$-PEO] was obtained.

0.1 mmole of the NPC-multiblock PEO obtained above, 0.2 mmole of tris (hydroxymethyl) aminomethane and DMSO as solvent were mixed and reacted for 24 hours. The reacted material was precipitated in ether, and the precipitated material was dissolved in water. After extracting using chloroform, the block polymer having hydroxyl groups at both ends was obtained. The hydroxyl groups of the obtained polymer show an NMR proton peak at 3.30 ppm (DMSO-d$_6$). The number average molecular weight of the obtained copolymer was 8,900.

EXAMPLE 16

The copolymer was obtained with the process of example 2 except that 0.1 mmole of the obtained copolymer of example 15 and 12 mmole of L-lactide were used. The number average molecular weight of the obtained copolymer was 24,000.

EXAMPLE 17

The copolymer was obtained with the process of example 1 except that 8 mmole of ε-caprolactone was used. The molecular weight of the obtained copolymer was 8,900.

EXAMPLE 18

The copolymer was obtained with the process of example 2 except that 0.1 mmole of the obtained copolymer of example 17 and 0.1 mmole of ε-caprolactone were used. The number average molecular weight of the obtained copolymer was 23,000.

We claim
1. A process for preparing a thermoplastic, biodegradable hydrogel multi-block copolymer for use as a drug delivery matrix comprising the steps of:
   i) preparing a hydrophilic block having a biodegradable linkage using a hydrophilic polymer selected from the group consisting of polyethyleneoxide having a number average molecular weight from 2,000 to 10,000 and a copolymer of polyethyleneoxide and polypropyleneoxide;
   ii) introducing hydroxyl groups to both ends of said hydrophilic block;
   iii) adding and polymerizing one or more monomers to form a hydrophobic block, said one or more monomers selected from the group consisting lactide, glycolide and caprolactone; and
   iv) adding and anion polymerizing monomers of ethyleneoxide.

2. A process for preparing a thermoplastic, biodegradable hydrogel multi-block copolymer for use as a drug delivery matrix according to claim 1, wherein the hydrophilic block having a biodegradable linkage is prepared by the steps
   i) anionizing ends of said hydrophilic polymer using an initiator selected from the group consisting of potassium naphthalene, sodium naphthalene, lithium diisopropylate, potassium-t-butylate, sodium-t-butylate, sodium hydroxide and/or potassium hydroxide;

ii) adding and polymerizing one or more hydrophobic monomers selected from the group consisting of glycolide, lactide and caprolactone into the anionized ends of the hydrophilic polymer to form a copolymer having anion ends; and iii) adding and polymerizing ethyleneoxide into the anion ends of said copolymer.

3. A process for preparing a thermoplastic, biodegradable hydrogel multi-block copolymer useful as a drug delivery matrix according to claim 1, wherein the hydrophilic block is reacted with a reagent selected from the group consisting of tris (hydroxyalkyl) aminomethane and dihydroxyalkyl aminomethane in order to link the hydrophobic block.

4. A process for preparing a thermoplastic, biodegradable hydrogel multi-block copolymer useful as a drug delivery matrix according to claim 3, wherein said alkyl portion of said tris (hydroxyalkyl) aminomethane and said dihydroxyalkyl aminomethane is a $C_1$–$C_5$ aliphatic compound.

5. A process for preparing a thermoplastic, biodegradable multi-block copolymer useful as a drug delivery matrix according to claim 3, wherein both ends of said hydrophilic block are protected by p-nitrophenyl-chloroformate before the introduction of said hydroxyl groups.

* * * * *

UNITED STATES PATENT AND TRADEMARK OFFICE
CERTIFICATE OF CORRECTION

PATENT NO. : 5,514,380
DATED : May 7, 1996
INVENTOR(S) : Soo S. SONG et al.

It is certified that error appears in the above-indentified patent and that said Letters Patent is hereby corrected as shown below:

| Column | Line |  |
|---|---|---|
| 4 | 14-15 and 20-23 | Change "the integer" to --an integer from-- |
| 4 | 52 | Before "NMR" delete "the". |
| 4 | 53 | After "peaks" delete "in". |

Signed and Sealed this

Third Day of December, 1996

Attest:

BRUCE LEHMAN

Attesting Officer     Commissioner of Patents and Trademarks